(12) United States Patent
Havel et al.

(10) Patent No.: US 9,474,507 B2
(45) Date of Patent: Oct. 25, 2016

(54) RECIPROCATING ULTRASOUND DEVICE

(71) Applicant: Muffin Incorporated, West Lafayette, IN (US)

(72) Inventors: William J. Havel, West Lafayette, IN (US); Peter S. McKinnis, West Lafayette, IN (US); Neal E. Fearnot, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 118 days.

(21) Appl. No.: 14/143,375

(22) Filed: Dec. 30, 2013

(65) Prior Publication Data

US 2014/0194743 A1 Jul. 10, 2014

Related U.S. Application Data

(60) Provisional application No. 61/748,773, filed on Jan. 4, 2013.

(51) Int. Cl.
*A61B 8/12* (2006.01)
*A61B 8/00* (2006.01)
*A61B 8/08* (2006.01)

(52) U.S. Cl.
CPC ............ *A61B 8/445* (2013.01); *A61B 8/0891* (2013.01); *A61B 8/12* (2013.01); *A61B 8/4461* (2013.01); *A61B 8/4466* (2013.01)

(58) Field of Classification Search
CPC .................................................... A61B 8/445
See application file for complete search history.

(56) References Cited

U.S. PATENT DOCUMENTS

| | | | |
|---|---|---|---|
| 2,790,095 A | 4/1957 | Peek et al. | |
| 4,811,617 A * | 3/1989 | Whiteman, Jr. | ........ F16H 19/04 192/21 |
| 5,237,884 A | 8/1993 | Seto | |
| 5,535,715 A | 7/1996 | Mouton | |
| 5,611,246 A | 3/1997 | Long et al. | |
| 6,354,814 B1 | 3/2002 | Kaufmann et al. | |
| 7,798,971 B2 | 9/2010 | Flesch et al. | |
| 8,214,010 B2 | 7/2012 | Courtney et al. | |
| 2007/0038110 A1* | 2/2007 | Flesch | ....................... A61B 8/12 600/459 |
| 2007/0167821 A1 | 7/2007 | Lee et al. | |
| 2008/0234716 A1 | 9/2008 | Kiester | |
| 2009/0088631 A1 | 4/2009 | Dietz et al. | |
| 2010/0179426 A1 | 7/2010 | Davies et al. | |
| 2010/0217125 A1* | 8/2010 | Kadokura et al. | ............ 600/443 |
| 2011/0237955 A1 | 9/2011 | Dietz et al. | |
| 2011/0263986 A1* | 10/2011 | Park et al. | .................... 600/462 |
| 2012/0108980 A1 | 5/2012 | Shilling et al. | |

OTHER PUBLICATIONS

International Search Report and Written Opinion issued in PCT/US2013/078245, dated Apr. 25, 2014.

* cited by examiner

*Primary Examiner* — Mark Remaly
(74) *Attorney, Agent, or Firm* — Woodard, Emhardt, Moriarty, McNett & Henry LLP (57) ABSTRACT

A device for internal ultrasound procedures includes a motor which rotates a drive shaft and an ultrasound transducer. A gearing assembly provides reciprocating rotational motion from a unidirectional motor. A cam assembly provides reciprocating pivotal motion to the transducer. Conductors can attach to the transducer and extend through the drive shaft.

28 Claims, 7 Drawing Sheets

RECIPROCATING ULTRASOUND DEVICE

REFERENCE TO RELATED APPLICATIONS

This application claims the benefit of U.S. Provisional Patent Application No. 61/748,773, filed Jan. 4, 2013, which is hereby incorporated by reference.

FIELD OF THE DISCLOSURE

This disclosure concerns devices and methods for using ultrasound within the body of a patient. In particular, it concerns features that allow for efficient reciprocation of an ultrasound beam in small body areas, such as within blood vessels.

BACKGROUND

Ultrasound technology has been used for therapeutic and diagnostic medical procedures, which can include providing imaging of internal portions of a body. Ultrasound procedures typically use a transducer assembly to transmit and/or receive signals. In some cases, a stationary transducer assembly can view a full image area due to the particular positioning or electronic steering of the multiple ultrasound elements in an array. In other designs three-dimensional ultrasound images may be acquired by one-dimensional arrays connected to a mechanical actuator, to move the arrays within the body. Such designs are expensive and can result in a device too large for some vascular or other uses. To achieve good image quality, array transducers must sequentially transmit and receive on many separate channels. That condition requires many expensive and bulky coaxial cables. Fewer coaxial cables can be used, but doing so reduces the quality of the image and image frame rate.

Designs have been proposed including a rotating transducer assembly. Data is obtained by the transducer assembly emitting sequential ultrasound pulses at changing rotational positions. Advantages of the single-element rotational design when compared to an array design include smaller catheter diameter, better image quality, possible higher center frequency, lower cost for the ultrasound imaging console, and less ring down artifacts (dead zone). However, these designs present problems with performing ultrasound procedures in a plane which is parallel to the catheter axis or when performing three-dimensional scans, as it is necessary to rotate the transducer about an axis perpendicular to the catheter axis. Because full 360° rotation in elevation is typically not desirable, reciprocal motion is required.

Single element designs can also include certain disadvantages, such as non-uniform rotational distortion (NURD). During imaging procedures including a single element design, the ultrasound element is typically rotated with a torque cable. Ultrasound pulses are emitted in an even-spaced time-sequential manner under the expectation of a uniform rotation rate of the ultrasound element. Each reflected ultrasound echo signal represents a portion or scan line of an image. An image processor assembles the data based on the assumption that the data points represent images from evenly-spaced pulses. However, it can be difficult to achieve a uniform rotation rate for the ultrasound element when using a torque cable as a driving means. The ultrasound element can be around one meter from the driving end of the torque cable. Ideally, the torque cable will have sufficient stiffness to provide uniform rotation at both ends while simultaneously allowing maneuverability. However, as a practical matter a sufficiently maneuverable torque cable creates a potential for delay in the transferring of torque from one end of the cable to the other, as the cable stores and releases elastic energy, which can cause the transducer assembly to rotate at a non-uniform rate even when the rotation source rotates at a uniform rate. The non-uniform rotation rate causes the resulting images to be distorted.

Thus, there is a need to have an ultrasound system design that could be integrated with a catheter, that is cost effective, small in size, and which produces images free from NURD artifacts and blocked viewing areas.

SUMMARY

One solution could be to use a motor which provides reciprocating motion of the transducer assembly on the catheter axis as well as on an axis perpendicular to the catheter axis which eliminates the need for a rotating mechanical/electrical coupling. However, providing a reciprocating motion with a motor necessitates a powerful motor and complex feedback control systems.

Among other things, there are disclosed embodiments of devices for use in internal ultrasound procedures and methods for making and using them. For example, a medical device includes a unidirectional rotary motor, a bidirectional ultrasound transducer, and a unidirectional-to-bidirectional gearing assembly operatively disposed between the motor and the transducer. Additionally, a device for internal ultrasound treatment can include a rotary motor operatively coupled with a drive shaft, wherein the drive shaft is positioned radially inward of the motor and extends substantially along a rotation axis, so that operation of the motor rotates the drive shaft around the rotation axis. A transducer assembly configured for transmitting and/or receiving ultrasound signals is included. A gearing assembly is configured to convert between unidirectional rotation and simultaneous reciprocating rotation and includes an internal gear and first and second external gears. The first and second external gears are interengaged with each other. The internal gear is positioned to rotate about the rotation axis. The gearing assembly is operatively coupled with the first drive shaft and the transducer. The internal gear has a first toothed portion and a first untoothed portion and is disposed so that during rotation of the internal gear the first toothed portion alternately engages the first and second external gears.

The device also can include a diametric first external gear and a diametric second external gear. The diametric first external gears positioned radially opposite to the first external gear and the diametric second external gear is positioned radially opposite to the second external gear. The diametric first external gear engages both second external gear and the diametric second external gear. The diametric second external gear engages both the first external gear and the diametric first external gear. The configuration of the external gears creates a radially central aperture which follows the rotation axis through the gearing assembly. The device can include a conduction pathway which extends from the transducer through the aperture.

The device can include a second drive shaft operatively disposed between the transducer and the gearing assembly. The first drive shaft can include a first lumen running therethrough and the second drive shaft can include a second lumen running therethrough. The first drive shaft can be operatively connected with the internal gear such that the conduction pathway extends from the transducer through the first and second lumens.

The device can include a third external gear and a driving gear such that the third external gear is disposed rotate coaxially and in response to rotation of the second external gear. The driving gear can be interengaged with the third external gear and disposed to rotate about the rotation axis. The driving gear can include a radially central hole such that the conduction pathway extends through the hole. The second drive shaft can be operatively connected with the driving gear.

The internal gear can include a second toothed portion positioned radially opposite of the first toothed portion. The first and second toothed portions can have an arc length (L) defined by the formula $L=\theta r$, where r is the radius measured from the rotation axis to toothed portion, and where $\theta \leq 90°$. The device can be mounted in a catheter. The device can be configured such that the transducer rotates reciprocatingly through a range of at least 360° in each direction.

An alternative embodiment of a device for internal ultrasound can include a first motor operatively coupled with a first drive shaft such that the first drive shaft extends substantially along a rotation axis and wherein operation of the first motor rotates the first drive shaft about the rotation axis. A transducer is configured for transmitting and/or receiving ultrasound signals and is disposed to rotate about a pivot axis which is substantially perpendicular to the rotation axis. The first drive shaft includes a cam surface disposed to impart pivotal motion to the transducer when the first drive shaft rotates. The device can include an elongated slot positioned to receive the cam surface such that the cam surface is positioned on a part of the first drive shaft which is bent at an angular offset relative to the rotation axis. The device can include a cam plate such that the elongated slot is situated in the cam plate and wherein the cam plate extends from a surface of the transducer.

The device can include a second motor operatively coupled with a second drive shaft which includes a lumen extending therethrough such that the second drive shaft extends substantially along the rotation axis and wherein operation of the second motor rotates the second drive shaft about the rotation axis. The transducer can be operatively connected with the second drive shaft such that a difference between the rotational speed of the first motor and the rotational speed of the second motor determines the rotational speed of the transducer about the pivot axis. The first and second drive shafts can be positioned concentrically. The first motor can be movable along the rotation axis such that movement of the first motor along the rotation axis changes the rotational range of motion of the transducer about the pivot axis.

Another embodiment of a device for internal ultrasound can include a transducer which is configured for transmitting and/or receiving ultrasound signals. The first motor is operatively disposed to impart rotational motion to the transducer about a pivot axis which is substantially perpendicular to a rotation axis. A second motor is operatively disposed to impart rotational motion to the transducer about the rotation axis. The rotational speed of the transducer about the pivot axis is determined by a difference between the rotational speed of the first motor and the rotational speed of the second motor. The first motor can be operatively coupled with a first drive shaft such that the first drive shaft extends substantially along the rotation axis and wherein operation of the first motor rotates the first drive shaft about the rotation axis. The second motor can be operatively coupled with a second drive shaft such that the second drive shaft extends substantially along the rotation axis and wherein operation of the second motor rotates the second drive shaft about the rotation axis. The transducer can be pivotally connected to the second drive shaft. The second drive shaft can be a hollow driveshaft such that the first and second drive shafts are positioned concentrically.

The first motor can be operatively coupled with the first drive shaft such that the first drive shaft extends substantially along the rotation axis and wherein operation of the first motor rotates the first drive shaft about the rotation axis. The first drive shaft can include a cam surface disposed to impart pivotal motion to the transducer when the first drive shaft rotates. The second motor can be operatively coupled with a second drive shaft such that the second drive shaft extends substantially along the rotation axis and wherein operation of the second motor rotates the second drive shaft around the rotation axis. The transducer can be pivotally connected to the second drive shaft. The device can include an elongated slot positioned to receive the cam surface such that the cam surface is positioned on the part of the drive shaft which is bent at an angular offset relative to the rotation axis. The device can include a cam plate, wherein the elongated slot is situated in the cam plate and wherein the cam plate extends from a surface of the transducer.

DESCRIPTION OF THE ILLUSTRATED EMBODIMENTS

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates.

Referring generally to the drawings, there are shown embodiments of a device 20 suitable for endoluminal medical procedures. Device 20 can be used with a system which includes a console (not shown) for processing data or signals received from an ultrasound transducer. The ultrasound console can be a type which is generally used for medical ultrasonic imaging, e.g. generally including control devices usable by a physician and a graphic display which displays graphical images obtained during an ultrasound procedure. Device 20 can be used for obtaining images at various locations of a body such as a blood vessel, urethra, ureter, vagina, rectum, throat, ear, or through an artificial tract (or lumen) by percutaneous puncture for example. The console portion can be connected to commercially available ultrasound probes or catheters with compatible pinout, or other medical devices which are configured for endoluminal procedures. Device 20 is capable of transmitting and receiving ultrasound signals and then communicating data obtained from ultrasound signals to the console.

Figure 1:
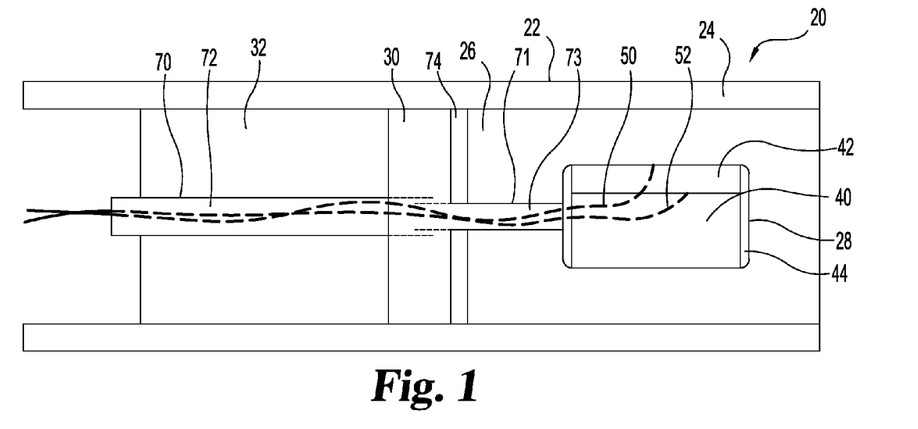
FIG. 1 is a schematic, partial cross-sectional view of an ultrasound imaging device having a gearing assembly.

In the embodiment shown schematically in FIG. 1, device 20 includes a catheter 22 or other flexible elongated member having a wall 24 defining an internal chamber 26. Catheter 22 is sized and configured for insertion into and/or travel along bodily orifices or lumens. Positioned within chamber 26 is a transducer 28, a gearing assembly 30, and a rotary motor 32 operatively coupled with transducer 28 through gearing assembly 30. Generally, catheter 22 carries transducer 28 to a bodily location where rotary motor 32 provides rotational motion to transducer 28. Device 20 could optionally include a motor housing (not shown) for providing structural support for rotary motor 32, gearing assembly 30, and transducer 28. Transducer 28 in conjunction with rotary motion provided by rotary motor 32 is capable of transmitting and receiving ultrasound signals in a variety of directions which are passed along data signal communication lines between transducer 28 and the ultrasound console.

Catheter 22 in the illustrated embodiment is an elongated device of plastic or other sturdy flexible material. Catheter 22 includes a control end which during use is nearest to the user and an application end which during use is nearest to the user's point of interest. The terms "control" and "application" are used throughout this description to describe these positional orientations. Wall 24 surrounds chamber 26, which is at the application end of device 20 in the illustrated embodiment. The control end of wall 24 and/or catheter 22 may extend outside of the patient during use (or may attach to another piece that extends outside the patient), and may end in a handle or other operating portion for maneuvering catheter 22. Particular embodiments of catheter 22 or at least chamber 26 are cylindrical, and are sized for insertion into and passage through bodily orifices and lumens, such as, for example, insertion into the femoral artery and passage through it toward the heart. Wall 24 may have a port or other feature to allow injection of fluid into chamber 26, as will be discussed further below.

Catheter 22 has at least a portion that presents a minimal barrier to the passage of ultrasound signals which is small enough that ultrasound images may be reasonably acquired through the barrier. Catheter 22 has at least a portion surrounding device 20 that is constructed of a material which is substantially echolucent (i.e. having small ultrasound attenuation, or having a small difference in acoustic impedance with the surrounding environment) when placed in the surrounding working environment such that it acts as an acoustic window which allows passage of ultrasound signals with minimal reflection. For example, when used within a blood vessel containing body tissues and blood, it is preferable for catheter 22 to be constructed of a material which is structurally rigid and which has acoustic impedance similar to that of body fluids such as blood. Possible materials could include, for example, a polymer material such as high density polyethelene, polymethylpentene (PMP), or acrylonitrile butadiene styrene (ABS). It has been determined that in some cases the thickness of at least the portion of catheter 22 which serves as the viewing window can be approximately N/2 (where N is a positive integer) of the wavelength corresponding to the center frequency of the ultrasound signal.

Transducer 28 is indicated schematically in the drawings. The term "transducer" should be understood to include an assembly of two or more parts as well as a single piece. An exemplary transducer 28 includes a body or backing 40 with at least one ultrasound element 42 attached to one side of backing 40, and one or more clamping rings 44. Transducer 28 can include a matching layer (not shown) attached to one side of element 42. Element 42 can be a piezoelectric element which has the ability to convert electrical energy into sound waves and sound waves into electrical energy. The positioning of element 42 as indicated, on a side of backing 40, results in a directed ultrasound beam direction. Backing 40 may be substantially opaque to ultrasound signals, so that such signals are effectively only projected outward from element 42, e.g. to one side or in a limited angular range radially (relative to a rotation axis) from backing 40. The matching layer has acoustic impedance generally between that of element 42 and the medium surrounding transducer 28 in order to minimize mismatched acoustic impedance between transducer 28 and the medium surrounding transducer 28. Transducer 28, as discussed, can be a single element transducer which is capable of sending and receiving ultrasound waves in a range of frequencies which are typically used in medical ultrasound procedures, such as, for example, in the range from 20 KHz to 100 MHz. In some examples, transducer 28 can include a linear array of elements extending along the rotation axis. Clamping rings 44 have been determined to improve efficiency and add mechanical stability to transducer 28.

Rotary motor 32 is a microminiature motor of a small size which is suitable for containment within chamber 26 of catheter 22. Microminiature motors such as small piezoelectric motors, electromagnetic motors, or shape memory motors may be used. In one embodiment, the motor is a three-phase, coreless, brushless DC electromagnetic motor, which has few components, small size and minimal complexity. Another embodiment includes a piezoelectric motor. Motor 32 is preferably of a small size, such as having a diameter in the range from 0.3 mm to 4 mm. The use of such microminiature motors at the application end of catheter 22 can eliminate problems with torque cables.

Device 20 includes rotatable shafts 70, 71 connecting transducer 28 and motor 32 via gearing assembly 30. Shaft 70 is coupled with motor 32 and rotates in response to rotation of the motor. Shaft 70 extends through the entirety of motor 32 in particular embodiments and is operatively coupled with gearing assembly 30. Shaft 71 is operatively coupled with transducer 28 so that transducer 28 rotates in response to rotation of shaft 71. Shaft 71 extends from transducer 28 and is operatively coupled with gearing assembly 30. Shafts 70, 71 can be hollow cylindrical shafts in the illustrated embodiment, having lumens 72, 73 extending therethrough. Lumens 72, 73 permit passage of electrical conductors, (e.g. wires, cables, guidewires), mechanical operational items (e.g. guidewires), and/or other features to pass through shafts 70, 71, allowing transmission of electrical and/or mechanical force or energy through lumens 72, 73 without affecting the rotation of shafts 70, 71.

Figure 2:
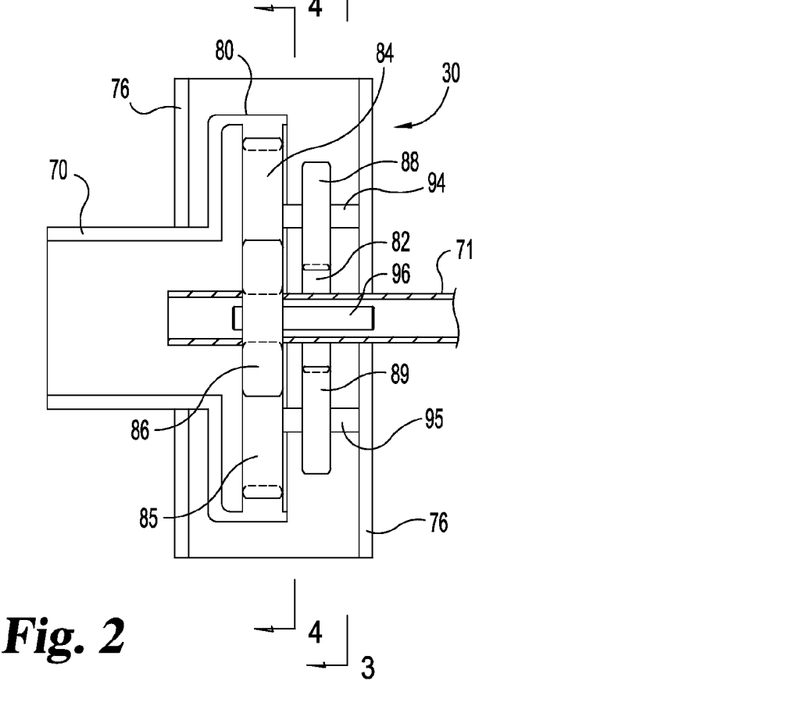
FIG. 2 is a schematic, partial cross-sectional view of a gearing assembly.
Figure 3:
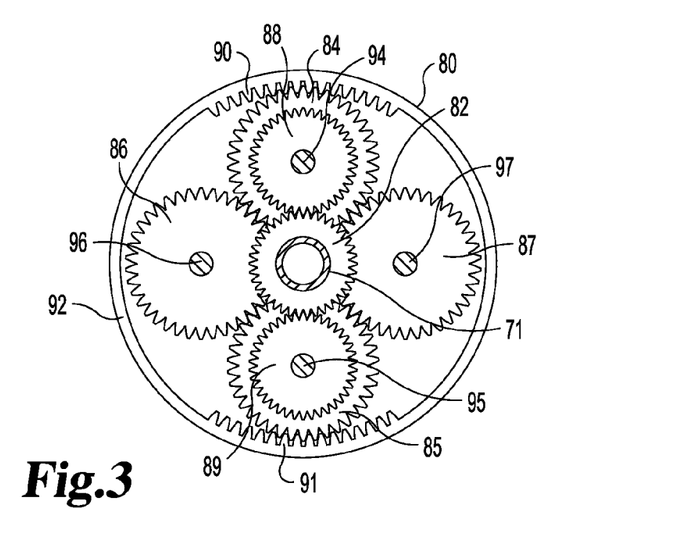
FIG. 3 is a cross-sectional view of the gearing assembly of FIG. 2 taken at the line 3-3.
Figure 4:
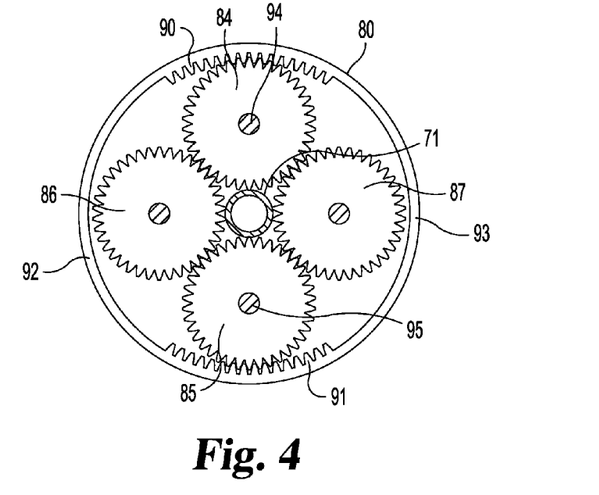
FIG. 4 is a cross-sectional view of the gearing assembly of FIG. 2 taken at the line 4-4.

In the embodiment of FIG. 1, gearing assembly 30 includes a housing 76 (FIGS. 2, 3). Housing 76 is disposed such that it is stationary or fixed relative to catheter 22. Gearing assembly 30 includes an arrangement of gears which are shown schematically in FIGS. 3 and 4. A ring gear 80 is coupled with shaft 70 and is configured to interact with first spur gears 84, 85 and second spur gears 86, 87. A driving gear 82 is coupled with shaft 71 and is configured to interact with third spur gears 88, 89. Gearing assembly 30 is configured to convert a unidirectional rotational motion into a reciprocating (or bidirectional) rotational motion. In one embodiment, gearing assembly 30 receives a substantially unidirectional rotational input from motor 32 and outputs a reciprocating rotational motion to transducer 28. Accordingly, gearing assembly 30 receives a substantially constant rotation input from shaft 70 and outputs a reciprocal rotation via shaft 71. A partial cross-sectional schematic diagram of an example of gearing assembly 30 is shown in FIG. 2. Shaft 70 couples with gearing assembly 30 on the control side of gearing assembly 30 and shaft 71 couples with gearing assembly 30 on the application side of gearing assembly 30.

Ring gear 80 is an internal gear, i.e., having teeth that point towards its rotation axis. Ring gear 80 is a type of gear which is sometimes called a sector gear or mutilated gear and which includes toothed portions 90, 91 (or sectors) and untoothed portions 92, 93. Toothed portions 90, 91 are positioned radially opposite to each other relative to the rotation axis. Each toothed portion 90, 91 occupies a portion of ring gear 80 which is no greater than one fourth of the circumference of ring gear 80. In other words, each toothed portion 90, 91 occupies a portion of ring gear 80 which has an arc length (L) defined by the formula $L=\theta r$, where r is the radius measured from the rotation axis to toothed portion 90, 91 and $\theta \leq 90°$ (or $\pi/2$ radians). Similarly, each untoothed portion 92, 93 occupies a portion of ring gear 80 which is no less than one fourth of the circumference of ring gear 80. Toothed portions 90, 91 may include a lead-in section positioned at one or both ends of each toothed portion 90, 91 (not shown). The lead-in section includes teeth which have a gradually reduced height (or length as measured radially) relative to the teeth positioned in the middle of toothed portions 90, 91. Ring gear 80 may be attached to shaft 70 or constructed as an integral portion of shaft 70 at the application side end of shaft 70. Ring gear 80 is depicted as part of a flange in FIG. 2. However, ring gear 80 may be incorporated with shaft 70 in a variety of configurations (e.g. shaft 70 may be larger than the diameter of ring gear 80). Shaft 70 may be supported by housing 76, or alternatively shaft 70 may be supported solely by motor 32.

The spur gears are external gears, i.e., having teeth that point away from their axes of rotation. First spur gears 84, 85 are coupled with shafts 94, 95 such that they rotate in response to rotation of shaft 94, 95. Second spur gears 86, 87 are coupled with shafts 96, 97 such that they rotate in response to rotation of shafts 96, 97. Shafts 94, 95, 96, 97 are rotatably supported by housing 76, which could include bearings, hubs, or other suitable rotational supports. First spur gear 85 is positioned diametrically opposite to first spur gear 84 relative to the rotation axis. Second spur gear 87 is positioned diametrically opposite to second spur gear 86 relative to the rotation axis. First spur gear 84 engages both second spur gears 86, 87. First spur gear 85 also engages both second spur gears 86, 87. The positioning of first spur gears 84, 85 and second spur gears 86, 87 creates a radially central aperture between the spur gears which can allow passage therethrough of shaft 71 in some embodiments (e.g. FIG. 4). Shaft 71 can be positioned such that a portion of its control side is concentric and/or adjacent to a portion of the application side end of shaft 70. Alternatively, shaft 71 need not pass through the aperture.

First spur gears 84, 85 are positioned such that at a rotational position of ring gear 80 when toothed portion 90 engages first spur gear 84, toothed portion 91 simultaneously engages first spur gear 85. When toothed portion 90 engages first spur gear 85, toothed portion 91 simultaneously engages first spur gear 84. When toothed portion 90 does not engage either of first spur gears 84, 85, toothed portion 91 also does not engage either of first spur gears 84, 85. Second spur gears 86, 87 are positioned such that at a rotational position of ring gear 80 when toothed portion 90 engages second spur gear 86, toothed portion 91 simultaneously engages second spur gear 87. When toothed portion 90 engages second spur gear 87, toothed portion 91 simultaneously engages second spur gear 86. When toothed portion 90 does not engage either of first spur gears 86, 87, toothed portion 91 also does not engage either of second spur gears 86, 87. In this way, at any given rotational position of ring gear 80, toothed portions 90, 91 either exclusively engage first spur gears 84, 85 or second spur gears 86, 87.

Third spur gear 88 is positioned on shaft 94 such that it rotates in response to rotation of first spur gear 84, on the application side of shaft 94 relative to first spur gear 84. Third spur gear 89 is positioned on shaft 95 such that it rotates in response to rotation of first spur gear 85, on the application side of shaft 95 relative to first spur gear 85. Third spur gears 88, 89 are positioned diametrically opposite each other relative to the rotation axis in this embodiment, and are positioned to engage with driving gear 82. Driving gear 82 is an external spur gear having a radially central hole which allows shaft 71 to be positioned therethrough. Driving gear 82 is fixedly connected to shaft 71 such that shaft 71 rotates in response to rotation of driving gear 82. In other embodiments, driving gears can be positioned offset from the rotation axis.

Operation of the gearing mechanism will now be described. Ring gear 80 is configured to receive a unidirectional rotational drive force from shaft 70. As shaft 70 rotates, for example, in a clockwise direction as seen in FIG. 3, ring gear 80 also rotates clockwise. When ring gear 80 rotates clockwise, toothed portions 90, 91 engage first spur gears 84, 85 and cause first spur gears 84, 85 to simultaneously rotate clockwise. First spur gears 84, 85 engage second spur gears 86, 87 and cause second spur gears 86, 87 to rotate counterclockwise. The clockwise rotation of first spur gears 84, 85 causes third spur gears 88, 89 to simultaneously rotate clockwise via shafts 94, 95. Clockwise rotation of third spur gears 88, 89 causes driving gear 82 and shaft 71 to rotate counterclockwise. As ring gear 80 continues to rotate clockwise, toothed portions 90, 91 disengage first spur gears 84, 85 and subsequently (or substantially simultaneously) engage second spur gears 86, 87, causing second spur gears 86, 87 to rotate clockwise. First spur gears 84, 85 responsively rotate counterclockwise. The counterclockwise rotation of first spur gears 84, 85 causes third spur gears 88, 89 to simultaneously rotate counterclockwise via shafts 94, 95. Counterclockwise rotation of third spur gears 88, 89 causes driving gear 82 and shaft 71 to rotate clockwise. As ring gear 80 continues to rotate clockwise, toothed portions 90, 91 disengage second spur gears 86, 87 and re-engage first spur gears 84, 85, which causes shaft 71 to again rotate counterclockwise. The lead-in section(s) of toothed portions 90, 91 minimizes or eliminates potential problems with jamming of the gears as toothed portions 90, 91 engagingly transition between first spur gears 84, 85 and second spur gears 86, 87. In this way, as shaft 70 is rotated in a uniform direction (which could be either clockwise or counterclockwise), shaft 71 undergoes reciprocal rotational motion.

Various aspects of gearing assembly 30 can be varied. For example, the arc lengths of tooth portions 90, 91 can be varied in order to allow for a moment during rotation of ring gear 80 when toothed portions 90, 91 do not engage either first spur gears 84, 85 or second spur gears 86, 87. Such a time period could allow energy to dissipate within gearing assembly 30 before re-engaging and reversing direction of the gears or be used as a feature for optimizing ultrasound imaging.

Additionally, the size of driving gear 82 can be varied in order to control the range of rotation of shaft 71 in each direction. Variations in the size of driving gear 82 necessitate an inverse variation in the size of third spur gears 88, 89. For example, driving gear 82 can have a reduced diameter while third spur gears 88, 89 have an increased diameter such that driving gear 82 maintains engagement with third spur gears 88, 89. Driving gear 82 can have a diameter which is substantially smaller than the diameter of third spur gears 88, 89 in order to provide for an increased range of rotation (or region) of shaft 71 (e.g. 360 degrees or more). Similarly, driving gear 82 can have a diameter which is substantially larger than the diameter of third spur gears 88, 89 in order to provide for a reduced range of rotation of shaft 71. A small range of rotation can limit the imaged volume but can improve frame rate and vice versa. In this way, the range of rotation could be small (e.g. 20°). For obtaining a complete slice, conical, or toroidal image, it is preferable that transducer 28 be rotated at least about 360 degrees in each direction.

It should be noted that gearing assembly 30 could include an assembly that does not have both third spur gears 88, 89, but rather has only one third spur gear (88 or 89). However, the addition of both third spur gears 88, 89 provide mechanical stability to gearing assembly 30.

Transducer 28 is operatively coupled with shaft 71 in this embodiment so that its longitudinal axis is parallel to or in some cases coincident with the rotation axis of shaft 71. An ultrasound beam or signals emitted from transducer 28 travel generally outward from the rotation axis in this embodiment. Similarly, transducer 28 receives an ultrasound beam or signals from directions outward of the rotation axis. Transducer 28 can be coupled directly to shaft 71. Alternatively, transducer 28 in one example could be coupled with shaft 71 through use of an intermediate support (not shown). The intermediate support can be hollow and defining an inner lumen in a similar manner as shaft 71. An intermediate support may be in the form of a gimbal mount or other type of support which provides pivoting (or elevational) rotational motion to the transducer, as explained in U.S. App. Ser. No. 61/713,172, incorporated herein by reference in its entirety.

A portion of chamber 26 immediately surrounding transducer 28 extending towards the application end of catheter 22 can be completely filled with a fluid or other substance having acoustic impedance similar to that of blood or tissue, such as saline, oils (e.g. mineral oil or castor oil), or mixed alcohol. A seal 74, bearing, or other structure is positioned adjacent to gearing assembly 30 and shaft 71 to provide a fluid seal between gearing assembly 30 and the chamber surrounding transducer 28. The substance should minimize friction acting against transducer 28 during rotation. In this way, acoustic matching can be achieved between body fluids, catheter 22, and the medium immediately surrounding transducer 28. Acoustic matching ensures that minimal signal losses occur when transmitting and receiving ultrasound signals between transducer 28 and body tissue which enhances the clarity of the resulting image. The fluid can be added to device 20 during manufacture, or alternatively could be added prior to use. When the transducer is sealed and the coupling fluid is placed into the chamber during manufacture, long term contact with the parts necessitates a non-corrosive fluid such as mineral oil or castor oil in order to preserve the shelf life of the product. Preferably, the oil is bio-compatible, acoustically transparent, and has low viscosity. Alternatively, a fluid communication port (not shown) may be positioned or creatable within the catheter or through the catheter wall to allow access for adding a fluid. In that case a corrosive fluid may be added at the time of deployment of device 20. Corrosive fluids such as water, saline, and alcohol typically have more favorable combinations of bio-compatibility, acoustic transparency and viscosity.

Device 20 is designed to pass an electrical signal from transducer 28 through lumens 72, 73. In the embodiment of FIG. 1, conductors 50, 52 are part of a conduction pathway which extends from transducer 28 through lumens 72, 73 and which is conductively operatively coupled with the console. For example, conductor 50 as a signal channel and conductor 52 as a ground channel. Conductors 50, 52 have an application side end attached to a rotating portion of the conduction pathway and a control side end (not shown) attached to a non-rotating portion of the conduction pathway, e.g. extending to a fixed conductor in the wall of catheter 22 or to the ultrasound console. Conductors 50, 52 can conduct electrical signals while passing through shaft 70 and undergoing a twisting motion in response to rotational motion from shaft 71 and transducer 28, without undergoing catastrophic damage.

As one example, conductors 50, 52 can be attached at a variety of locations to transducer element 42, depending on the requirements of the particular configuration. Conductors 50, 52 can be thin wires which extend through backing 40 and/or clamping rings 44 and into lumen 73. Alternatively, conductors 50, 52 can extend from the sides of transducer 28 and sealingly enter lumen 73 through a sealed port (not shown). Alternatively, backing 40 can be conductive so that the whole backing is part of the conduction path. Similarly, the matching layer could be a conductive layer which is part of the conduction path. Conductors 50, 52 may run throughout the length of the lumen of catheter 22 from transducer 28 to the ultrasound console. Alternatively, conductors 50, 52 could extend to an intermediate coupler (not shown) or control side attachment point located within catheter 22. The control side attachment point or coupler facilitates electrical communication between conductors 50, 52 and the ultrasound console. The control side attachment point is generally fixed in a non-rotational position which is on the control side of the control side end of the drive shaft 70. However, in some examples, the control side attachment point could be positioned within the hollow drive shaft. In other examples, conductors 50, 52 could be fixed into a single cable, which could be coaxial, for example. In other examples, conductors 50, 52 could be coupled with one or more intermediate conductors (for example a rigid shaft or single cable) positioned between transducer 28 and conductors 50, 52. In this way, a conduction path is achieved in a variety of ways in which the conduction path extends through lumens 72, 73 and includes conductors 50, 52.

During operation of device 20, a physician inserts device 20 into the body of a patient and maneuvers it to a desired location, e.g. in a particular blood vessel. Once device 20 is properly positioned in or near the area of body tissue which is to be imaged, rotary motor 32 is powered such that shaft 70 rotates. Correspondingly, shaft 71 and transducer 28 rotate about the rotation axis. Transducer 28 is energized through the conduction pathway (e.g. conductor 50), which receives power from the console. Transducer 28 transmits an ultrasound signal substantially in an outward direction relative to shaft 71 in this embodiment, i.e. substantially perpendicular to the rotation axis.

When an ultrasound signal is transmitted, the ultrasound signal passes across wall 24 of catheter 22 until it encounters an acoustic impedance boundary (e.g. body tissue, plaque, medical implant, or other material which has acoustic impedance sufficiently different from bodily fluids or other surrounding material) such that the ultrasound signal is at least partially reflected at the boundary. At lease a portion of the ultrasound signal is reflected back towards transducer 28. One or more electrical signals representing reflected ultrasound received at transducer 28 are sent from transducer 28 via the conduction pathway (e.g. conductor 50) to the ultrasound console, for imaging and display to the physician. Simultaneously or subsequently transducer 28 continues to emit further ultrasound signals and the process is repeated, continuously in certain embodiments over a desired period of time.

Transducer 28 is rotated in a reciprocating manner under the power of rotary motor 32 via gearing assembly 30 such that it is rotated a fixed distance in one direction and then rotated a fixed distance in the opposite direction. In the FIG. 1 example, conductors 50, 52 rotate in sync with transducer 28 and in particular embodiments become at least partially twisted around each other in one direction, untwisted, and at least partially twisted around each other in the opposite direction (e.g. 360 degree twist clockwise, 360 degree untwist counterclockwise, 360 degree twist counterclockwise, and 360 degree untwist clockwise). The control side connection point (not shown) of the conductors 50, 52 remains stationary, which facilitates controlled twisting of the conductors as well as allowing a non-rotating coupling with the console. Conductors 50, 52 are positioned within the lumens 72, 73 with sufficient slack to allow conductors 50, 52 to become wound without damaging either conductors 50, 52 or their connection points with transducer 28 or the control side connection point. In other examples, conductors 50, 52 could be fixed into a single cable (e.g. coaxial) which is constructed with elastic (or other) characteristics which allow some twisting of the cable without undergoing catastrophic damage to the conductors. In still other examples, conductors 50, 52 are configured to undergo a twisting reaction when attached to an intermediate conductor conductively operatively positioned between element 42 and conductors 50, 52.

Figure 5:
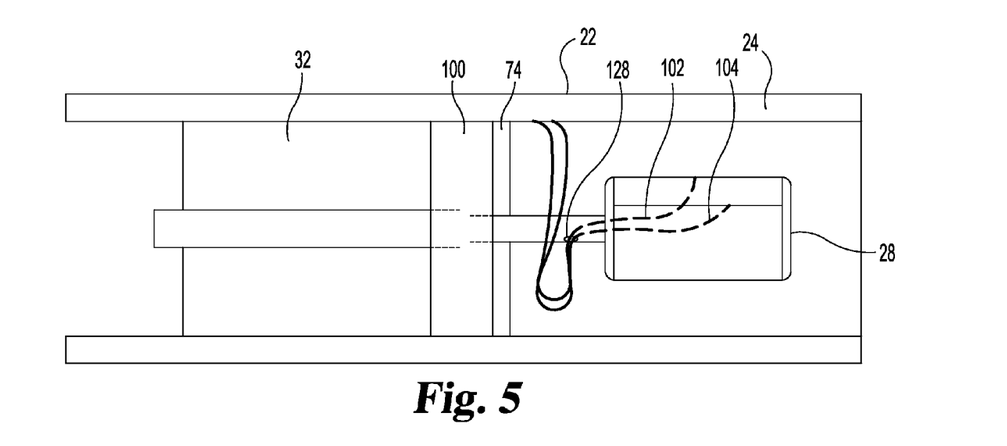
FIG. 5 is a schematic, partial cross-sectional view of an ultrasound imaging device having a gearing assembly.

An alternative embodiment of device 20 is shown in FIG. 5. Device 20 includes transducer 28, gearing assembly 100, and motor 32. Device 20 is similar to the FIG. 1 embodiment and functions in the same way with the notable exception of gearing assembly 100 and the conduction pathways (including conductors 102, 104). Device 20 includes rotating shafts 70, 71 for operable connection between motor 32, gearing assembly 100, and transducer 28. In this embodiment, shaft 70 may or may not include a lumen.

Figure 6:
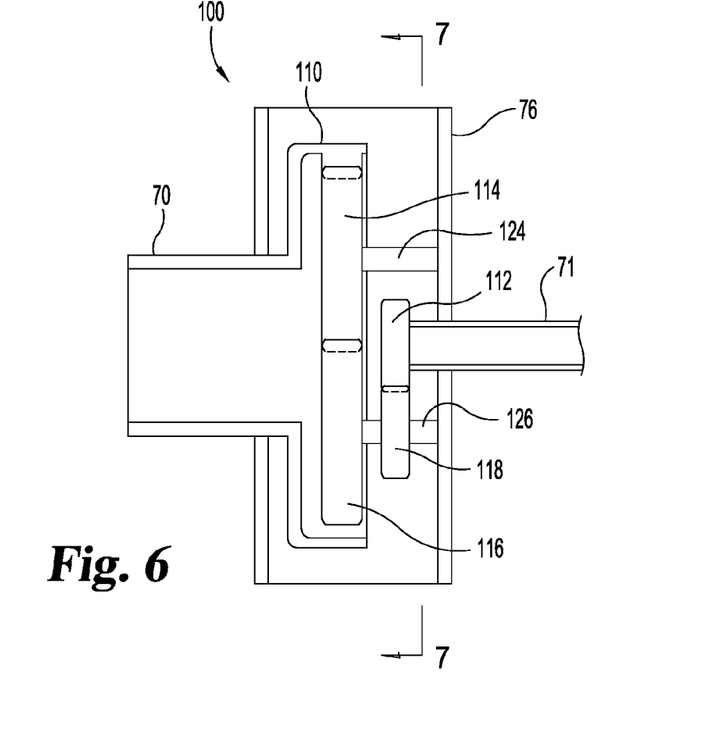
FIG. 6 is a schematic, partial cross-sectional view of a gearing assembly.

Gearing assembly 100 is configured to receive a constant rotational input from motor 32 and output a reciprocating rotation to transducer 28. A part cross-sectional schematic diagram of gearing assembly 100 is shown in FIG. 6. Shaft 70 couples with gearing assembly 100 on the control side of gearing assembly 100 and shaft 71 couples with gearing assembly 100 on the application side of gearing assembly 100. Gearing assembly 100 includes a housing 76. Housing 76 is disposed such that it is stationary or fixed relative to catheter 22. Gearing assembly 100 includes an arrangement of gears which are shown schematically in FIG. 7. A ring gear 110 is coupled with shaft 70 and is configured to interact with first spur gear 114 and second spur gear 116. The driving gear 112 is coupled with shaft 71 and is configured to interact with third spur gear 118.

Ring gear 110 is an internal gear, i.e. having teeth that point towards its rotation axis. Ring gear 110 is a type of gear which is sometimes called a sector gear or mutilated gear and which includes a toothed portion 120 (or sector) and untoothed portion 122. Toothed portion 120 occupies a portion of ring gear 110 which is no greater than one half of the circumference of ring gear 110. In other words, toothed portion 120 occupies a portion of ring gear 110 which has an arc length defined by the formula $L=\theta r$, where r is the radius measured from the rotation axis to toothed portion 120 and $\theta \leq 180°$. Similarly, toothed portion 122 occupies a portion of ring gear 110 which is no less than one half of the circumference of ring gear 110. Toothed portion 120 may include a lead-in section (not shown) positioned at one or both ends of toothed portion 120. The lead-in section includes teeth which have a gradually reduced height (or length as measured radially) relative to the teeth positioned in the middle of toothed portion 120. Ring gear 110 may be attached to shaft 70 or constructed as an integral portion of shaft 70 at the application side and of shaft 70. Ring gear 110 is depicted as part of a flange in FIG. 6. However, ring gear 110 may be incorporated with shaft 70 in a variety of configurations.

Figure 7:
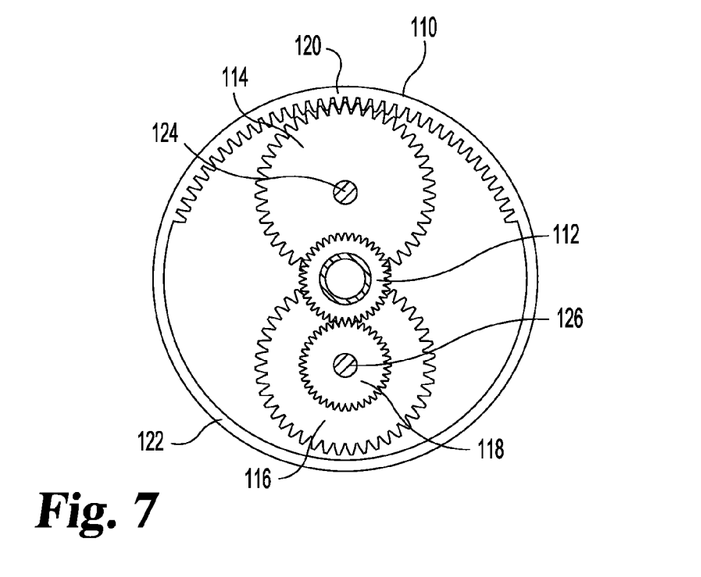
FIG. 7 is a cross-sectional view of the gearing assembly of FIG. 6 taken at the line 7-7.

Spur gears 114, 116, 118 are external gears, i.e. having teeth that point away from their respective rotation axis. First spur gear 114 is coupled with shaft 124 such that it rotates in response to rotation of shaft 124. Second spur gear 116 is coupled with shaft 126 such that it rotates in response to rotation of shaft 126. Shafts 124, 126 are rotatably supported by housing 76, which could include bearings, hubs, or other suitable rotational supports. Gears 114, 116 are positioned diametrically opposite to each other and disposed such that first spur gear 114 engages second spur gear 116. First spur gear 114, second spur gear 116, and toothed portion 120 are arranged and configured such that toothed portion 120 can exclusively engage either spur gear 114 or spur gear 116, but not both simultaneously. Third spur gear 118 is positioned on shaft 126 such that it rotates in response to rotation of second spur gear 116. Third spur gear 118 is positioned on the application side of shaft 126 relative to second spur gear 116. Driving gear 112 is an external gear and is fixedly attached to shaft 71 such that shaft 71 rotates in response to rotation of driving gear 112.

Ring gear 110 is configured to receive a unidirectional rotational drive force from shaft 70. When ring gear 110 rotates in a clockwise direction as seen in FIG. 7, toothed portion 120 engages first spur gear 114 and causes first spur gear 114 to simultaneously rotate clockwise about the axis of shaft 124. First spur gear 114 engages second spur gear 116 and causes second spur gear 116 to rotate counterclockwise about the axis of shaft 126. The counterclockwise rotation of second spur gear 116 causes third spur gear 118 to simultaneously rotate counterclockwise about shaft 126. Counterclockwise rotation of third spur gear 118 causes driving gear 112 and shaft 71 to rotate clockwise. As ring gear 110 continues to rotate clockwise toothed portion 120 disengages from first spur gear 114 and subsequently engages second spur gear 116, causing second spur gear 116 to rotate clockwise. First spur gear 114 responsively rotates counterclockwise. The clockwise rotation of second spur gear 116 causes third spur gear 118 to simultaneously rotate clockwise via shaft 126. Clockwise rotation of third spur gear 118 causes driving gear 112 and shaft 71 to rotate counterclockwise. As ring gear 110 continues to rotate clockwise, toothed portion 120 disengages second spur gear 116 and subsequently re-engages first spur gear 114 which causes shaft 71 to again rotate clockwise. The lead-in section(s) of toothed portion 120 minimizes or eliminates any potential problems with jamming of the gears as toothed portion 120 engagingly transitions between first spur gear 114 and second spur gear 116. In this way, as shaft 70 is rotated in a unidirectional direction (which could be either clockwise or counterclockwise), shaft 71 undergoes reciprocal rotational motion.

Various aspects of gearing assembly 100 can be varied as previously described for the FIG. 1 embodiment, such as variations in the arc length of toothed portion 120 and in the size of driving gear 112 and to the same effect as described herein.

In the FIG. 5 embodiment, conductors 102, 104 pass from transducer 28 to wall 24 and run along wall 24 to conductively couple with the console. Conductors 102, 104 can pass first into hollow shaft 71 and exit through opening 128. Alternatively, conductors 102, 104 can couple with transducer 28 at a location which is external to hollow shaft 71. Conductors 102, 104 are positioned with sufficient access between transducer 28 and an attachment point at wall 24 such that when shaft 71 rotates, conductors 102, 104 alternately twist and untwist about shaft 71. For example, if it is desirable for transducer 28 to rotate 720° sequentially in each direction, conductors 102, 104 will have sufficient excess in order to wrap about shaft 71 for at least a full 360° rotation in each rotational direction from a neutral start point.

The embodiment of FIG. 1 can be combined with the conductor arrangement of FIG. 5. In that case, lumen 73 of shaft 71 could accommodate other components, such as a guidewire for example. In one example, a guidewire could extend through lumen 72 of the motor shaft 70, through lumen 73 of shaft 71, past (or through) transducer 28, and through the catheter tip. In some embodiments, lumens 72, 73 could accommodate both a guidewire and conductors.

Figure 14:
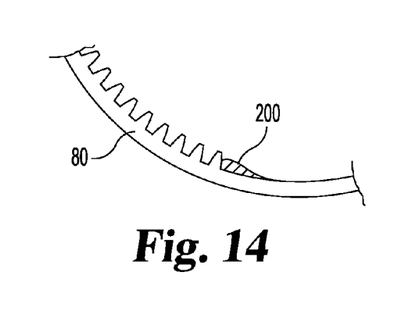
FIG. 14 is a schematic, partial cross-sectional view of a ring gear having a lobe positioned adjacent to a toothed portion.

Alternatively or in conjunction with the toothed portion lead-in sections of various embodiments described herein, a frictional interface can be added between the spur gears and the ring gear. In one embodiment, a lobe 200 is positioned adjacent to the end of the toothed portions (FIG. 14). Lobe 200 is a raised hump attached to the ring gear and is constructed in particular cases from a resiliently compressible material, such as rubber for example. During operation, as the ring gear disengages the first or second spur gears and engages the second or first spur gears (respectively), lobe 200 absorbs some of the energy (or momentum) of the spur gear as it changes direction. Lobe 200 frictionally engages the spur gear and causes it to reverse direction (or start rotating) such that it rotates at a proper speed to engage the ring gear.

Figure 15:
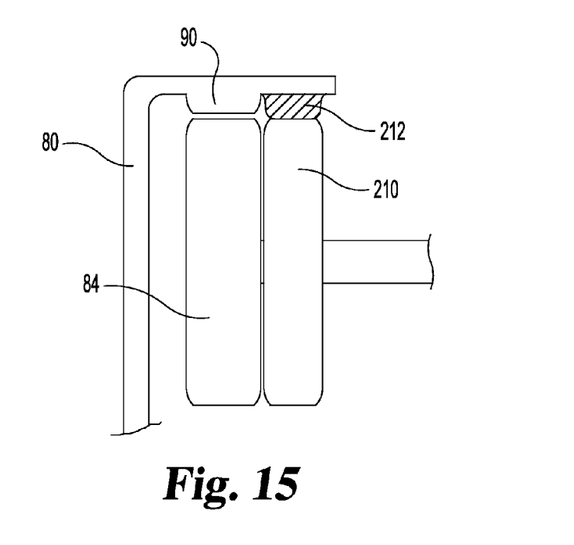
FIG. 15 is a schematic, partial cross-sectional view of a gearing assembly including a lobe and disc structure.

An alternative embodiment includes one or more non-toothed discs 210 positioned adjacent with and connected to the spur gears such that it rotates in response to rotation of the spur gear (FIG. 15). In this embodiment, a lobe 212 is positioned at an axial offset relative to the teeth in the toothed portions of the ring gear. Disc 210 can also be constructed from a resiliently compressible material, or alternatively it can be constructed from a relatively rigid material. During operation, as the ring gear disengages and re-engages the spur gears, disc 210 frictionally engages lobe 212 which causes disc 210 and the spur gear to reduce rotational speed and change direction prior to toothed gearing engagement between the ring gear and the spur gear. The embodiments of FIGS. 14 and 15 serve the purpose of smoothly reversing velocity of the spur gears without impacting and damaging the gear teeth. In other words, the gears are protected from damage which might otherwise be caused from engagement of the gears while rotating in opposing directions. In this way, lobe 200, lobe 212, and disc 210 serve a function similar to that of a synchronizer in a manual transmission gearbox.

Figure 11:
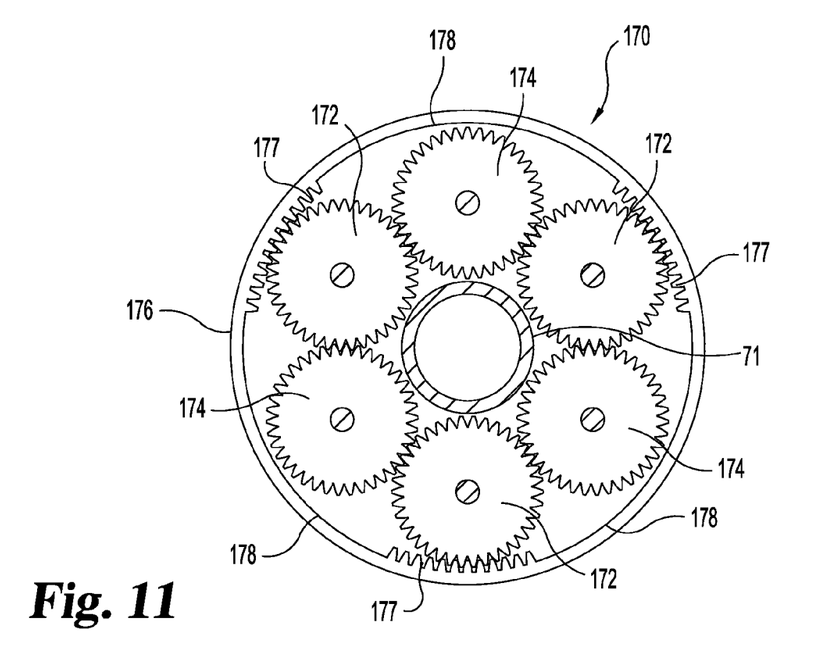
FIG. 11 is a cross-sectional view of a gearing assembly.

A further alternative gearing assembly embodiment is shown in FIG. 11. Gearing assembly 170 is similar in many aspects to previously described gearing assembly 30. Gearing assembly 170 includes three first spur gears 172, three second spur gears 174, and ring gear 176. Ring gear 176 includes three toothed portions 177 and three untoothed portions 178. When ring gear 176 rotates unidirectionally about the rotation axis, toothed portions 177 alternatingly engage first spur gears 172 and second spur gears 174. The alternating engagement causes reciprocal motion of the first and second spur gears from which a third spur gear can translate the reciprocal motion to a driving gear (not shown). The use of six spur gears allows the use of spur gears having reduced diameters and correspondingly the spur gears occupy less area near the center of the ring gear. Accordingly, shaft 71 can be made with a larger diameter and a larger lumen 73 which can accommodate larger diameter conductors, greater numbers of conductors (e.g. for a transducer having a linear array), and/or a larger guidewire. Gearing assembly 170 could also include an arrangement of eight spur gears, having four first spur gears, four second spur gears, and four toothed sections. Similarly, gearing assembly 170 could include an arrangement having ten or more spur gears wherein the number of spur gears is an even number.

Figure 12:
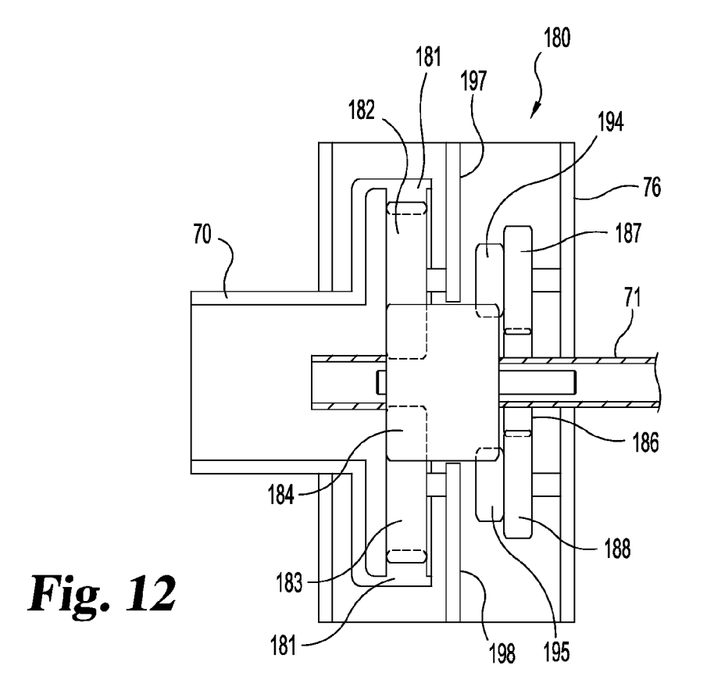
FIG. 12 is a schematic, partial cross-sectional view of a gearing assembly.
Figure 13:
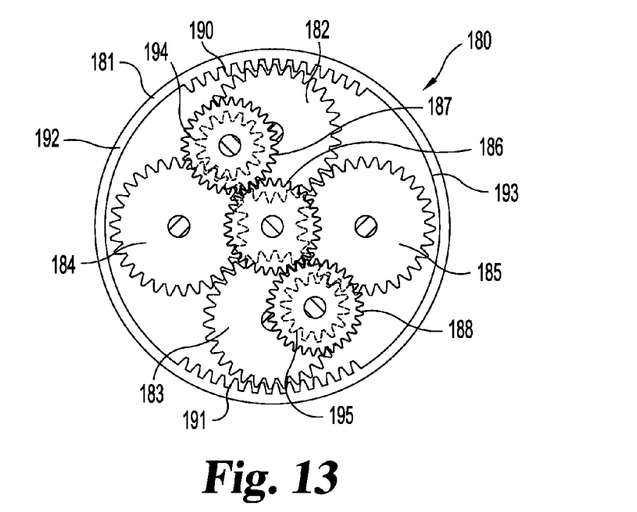
FIG. 13 is a schematic, partial cross-sectional view of the gearing assembly of FIG. 12.

A further alternative gearing assembly embodiment is shown in FIGS. 12 and 13. In that embodiment, gearing assembly 180 is configured to receive a constant rotational input from motor 32 and output a reciprocating rotation to transducer 28. A part cross-sectional schematic diagram of gearing assembly 180 is shown in FIG. 12. Shaft 70 couples with gearing assembly 180 on the control side of gearing assembly 180 and shaft 71 couples with gearing assembly 180 on the application side of gearing assembly 180. Gearing assembly 180 includes a housing 76 which is disposed such that it is fixed relative to catheter 22.

Gearing assembly 180 includes an arrangement of gears which are shown schematically in FIG. 13. In that example, a ring gear 181 is coupled with shaft 70 and is configured to interact with first spur gears 182, 183 and second spur gears 184, 185. A driving gear 186 is coupled with shaft 71 and is configured to interact with third spur gears 187, 188. Ring gear 181 is an internal gear having two toothed portions as described for the FIG. 2 embodiment. First spur gears 182, 183 are external gears as described for the FIG. 2 embodiment. First spur gears 182, 183 can be rotatably attached to gear supports 197, 198 which are fixed to (or relative to) housing 76. Second spur gears 184, 185 are external gears having a width which is greater than the width (or length measured along the central axis of the gear) of first spur gears 182, 183. Fourth spur gears 194, 195 are fixedly attached to third spur gears 187, 188 and rotate in unison with third spur gears 187, 188. The third and fourth spur gears are rotatably mounted to a housing 76 on rotation axes which are not parallel to the rotation axes of first spur gears 182, 183 (FIG. 13). Fourth spur gear 194 is positioned to engage second spur gear 184. Fourth spur gear 195 is positioned to engage second spur gear 185. Driving gear 186 is positioned to engage third spur gears 187, 188.

Gearing assembly 180 provides 360° reciprocal rotation to shaft 71 while also providing a lumen through shaft 71 to accommodate a plurality of conductors and/or a guidewire. Fourth spur gears 194, 195 can include reduced diameter and a reduced number of teeth (compared to third spur gears 187, 188) in order to increase the gear ratio between second spur gears 184, 185 and fourth spur gears 194, 195. The increased gear ratio causes fourth spur gears 194, 195 to undergo multiple full rotations (or more than one full rotation) for each full rotation of second spur gears 184, 185. Because fourth spur gears 194, 195 are attached to third spur gears 187, 188, third spur gears 187, 188 also undergo multiple full rotations for each full rotation of second spur gears 184, 185. The gear ratio between third spur gears 187, 188 and driving gear 186 can also be modified by enlarging or reducing the diameter of third spur gears 187, 188 and enlarging or reducing the diameter of driving gear 186. In this way, gear ratios can be achieved in which shaft 71 rotates a full 360° in a single direction in response to a single engagement (or approximately 90° rotation of ring gear 181) between toothed portions 190, 191 (separated by and untoothed portions 192, 193) and either first spur gears 182, 183 or second spur gears 184, 185.

The axes of rotation of fourth spur gears 194, 195 (and third spur gears 187, 188) can be moved further from the rotation axis in order to accommodate a larger lumen 73 through shaft 71 while maintaining engagement between fourth spur gears 194, 195 and second spur gears 184, 185. The lumen can be further enlarged by combining the FIG. 12 example with gearing assemblies having more than four spur gears for engagement with the ring gear (e.g. FIG. 11).

Figure 8:
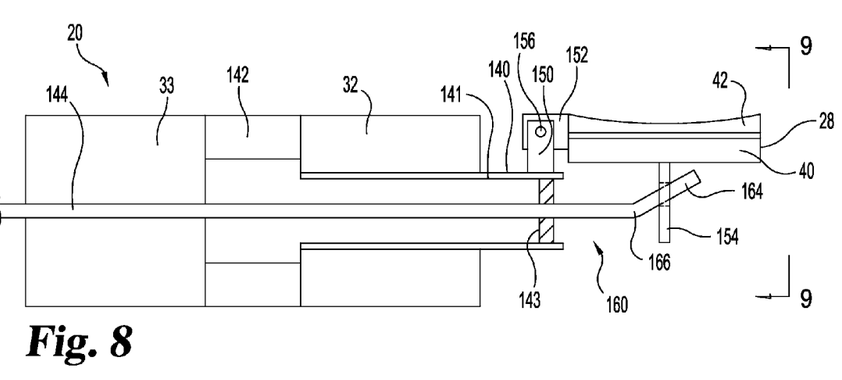
FIG. 8 is a schematic, partial cross-sectional view of an ultrasound imaging device having a pivoting assembly.
Figure 9:
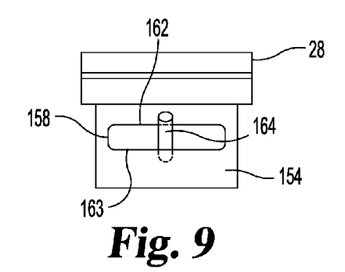
FIG. 9 is a partial front schematic view of a transducer 28 and pivoting assembly taken at the line 9-9.
Figure 10:
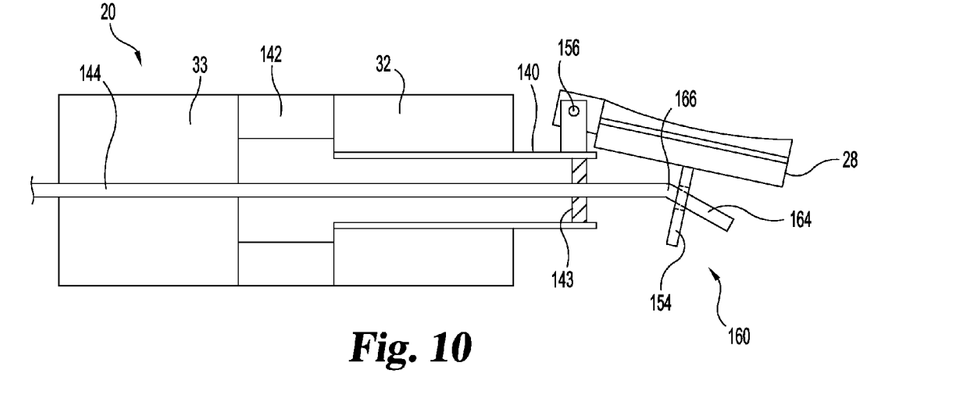
FIG. 10 is a schematic, partial cross-sectional view of an ultrasound imaging device having a pivoting assembly and a pivoted transducer.

A further alternative embodiment of device 20 is shown in FIGS. 8 through 10. Device 20 includes rotary motors 32, 33, catheter 22 (not shown), shaft 140, transducer 28, and bias force member 142. Transducer 28 is pivotally mounted to shaft 140 such that device 20 provides an ultrasound signal sweep or field that not only turns around the rotation axis of device 20 but also is pivotable to view forward and/or rearward of the particular position of transducer 28. A pivot assembly 160 includes pivot mount 150, transducer mount 152, cam plate 154, and bent shaft 144. Pivot assembly 160 provides reciprocal movement of transducer 28 about a pivot axis between a neutral position and a maximum displacement position.

Rotary motors 32, 33 are microminiature motors as previously described. Rotary motor 32 is coupled with shaft 140 and causes shaft 140 to rotate about the rotation axis. Shaft 140 is a hollow cylindrical shaft having a lumen 141 extending therethrough. Rotary motor 33 is coupled with bent shaft 144 and causes bent shaft 144 to rotate about the rotation axis. Bent shaft 144 extends from motor 33 through lumen 141. Bent shaft 144 can be supported near the application side end of shaft 140 by a bearing 143. A bias force member 142 is positioned between motor 32 and motor 33 and is connected to motors 32, 33 such that it causes a biasing force which tends to pull motor 33 towards motor 32. Bias force member 142 can be a coiled spring, elastic rubber member, or other suitable biasing member.

Pivot mount 150 is coupled with shaft 140 such that it rotates in response to rotation of shaft 140. Pivot mount 150 is configured to accept pin 156. Transducer mount 152 is fixedly coupled with transducer 28 and configured to receive pin 156. Transducer mount 152 is rotationally coupled with pivot mount 150 via pin 156 such that transducer mount 152 is rotatable relative to pivot mount 150 and shaft 140. Pin 156 defines a pivot axis about which transducer 28 is pivotable. Pivot mount 150 can include a slot configured to receive transducer mount 152 such that two extending members couple to two opposite sides of transducer mount 152 (not shown). Alternatively pivot mount 150 can be a member which connects to a single side of transducer mount 152 (FIG. 8).

Cam plate 154 is attached to the bottom of transducer 28 (e.g. backing 40) such that it is positioned substantially parallel (but not necessarily coincident) to the pivot axis. Cam plate 154 operates as a cam follower. Cam plate 154 includes an elongated slot 158 which is generally parallel to the pivot axis. The elongated slot 158 includes top surface 162 and bottom surface 163. Bent shaft 144 includes bent end 164. Bent end 164 includes the portion of bent shaft 144 which extends in a direction which is angularly offset from the rotation axis (i.e. the portion of shaft 144 which is on the application side of bend 166). Bent end 164 is configured to pass through the elongated slot 158. Bent end 164 has surfaces which act as cam surfaces and which are configured to engage top surface 162 and/or bottom surface 163 depending on the rotational position of bent shaft 144.

Pivot assembly 160 permits a reciprocating pivotal motion for transducer 28. Motor 33 is capable of rotating bent shaft 144 about the rotation axis. When bent shaft 144 rotates about the rotation axis relative to shaft 140 (and likewise cam plate 154), bent end 164 engages cam plate 154 and causes transducer 28 to pivot reciprocally about the pivot axis. Rotation of bent shaft 144 causes bent end 164 to rotate about the rotation axis between a zero displacement position (FIG. 8) and a maximum displacement position (FIG. 10). In the zero displacement position, bent end 164 is generally closer to the pivot axis than when in the maximum displacement position. However, the distance from the pivot axis to elongated slot 158 does not vary between the maximum displacement position and the zero displacement position. Thus, bent end 164 is situated differently within slot 158 between the zero and maximum displacement positions in a generally axial direction relative to the rotation axis.

In the configuration of FIG. 8, bent shaft 144 is in a neutral position and bent end 164 is in the zero displacement position, i.e. transducer 28 is positioned with a transmitting angle that is substantially perpendicular to the rotation axis. In that configuration a portion of bent end 164 abuts against top surface 162 and/or bottom surface 163. As bent shaft 144 rotates 90° clockwise (relative to FIG. 9) between the zero displacement position and the maximum displacement position, bent end 164 moves in a generally radial direction (relative to the rotation axis) within slot 158 from a central position towards an end of slot 158. The abutment of bent end 164 against surfaces 162, 163 and the positioning of bent end 164 further from the pivot axis causes cam plate 154 and transducer 28 to pivot about the pivot axis in a direction which is towards the rotation axis (i.e. clockwise relative to FIG. 8).

As bent shaft 144 rotates a further 90° clockwise, bent end 164 moves to the maximum displacement position. Simultaneously, bent end 164 moves in a generally radial direction (relative to the rotation axis) within slot 158 back towards the central position within slot 158. Surfaces 162, 163 slide along bent end 164 generally in the control side direction of bent shaft 144 to accommodate the relative difference in distances from the pivot axis to slot 158 and bent end 164. The abutment of bent end 164 against surfaces 162, 163 and movement of bent end 164 towards the maximum displacement point cause transducer 28 to pivot further about the pivot axis towards the rotation axis. During rotation as bent shaft 144 rotates further 90° clockwise, bent end 164 again moves in a generally radial direction (relative to the rotation axis) within slot 158, and bent end 164 returns to an intermediate position between the zero displacement position and the maximum displacement position. Simultaneously, transducer 28 moves from a maximum displacement position to an intermediate displacement position. A further 90° rotation causes bent shaft 144 to return to the zero displacement position and transducer 28 resumes the neutral position. In this way, pivot assembly 160 provides reciprocal pivoting motion to transducer 28 based on uniform rotation of motor 33.

When combined with the rotational motion of shaft 140, transducer 28 is movable about both the pivot axis and the rotation axis. The rate of pivoting motion is controlled by a speed difference (or phase difference) between motor 32 and motor 33. For example, when motor 32 and motor 33 rotate at the same rate, transducer 28 undergoes rotation about the rotation axis only, as bent shaft 144 does not change position relative to the pivot axis. When motor 33 rotates while motor 32 is stationary, transducer 28 undergoes movement about the pivot axis only. When motor 32 rotates while motor 33 is stationary (or rotating at a different angular velocity), transducer 28 undergoes movement about both the rotation axis and the pivot axis. In this configuration, the relative speed of pivoting movement relative to rotation about the rotation axis is maximized (with the exception of causing motor 33 and motor 32 to rotate in opposite directions). The relative speed of pivoting movement relative to rotation about the rotation axis can be reduced by engaging motor 33 and causing it to rotate simultaneously with motor 32. The pivot speed is reduced as the difference in rotation speed between motor 32 and motor 33 is reduced. Similarly, the pivot speed is increased as the difference in rotation rates between motor 32 and motor 33 is increased. In other words, when motor 32 and motor 33 rotate at different angular velocities a phase difference accumulates between the rotational rate of bent shaft 144 and the rotational rate of transducer 28 about the pivot axis.

Controls for motors 32 and/or 33 may be provided to maintain one or both at a particular rotational speed or pattern. For example, modalities such as a spin around the rotation axis of between 30-100 Hz may be combined with a slower pivoting around the pivot axis of about 1-2 Hz, to provide clear images forward and backward in a defined pattern. It has also been determined that a relatively slow spin around the rotation axis (e.g. about 1-2 Hz) combined with pivoting around the pivot axis more rapidly, e.g. near a resonant frequency of device 20 can provide good results. A modality providing a faster rotation around the rotation axis when transducer 28 is pointed closer to the rotation axis and slower rotation around the rotating axis when transducer 28 is further from the rotating axis is also useful for improving the image frame rate and clarity.

The pivot range and speed of motion about the pivot axis relative to the rotation speed of motor 33 can be controlled by varying the configuration and/or size of bent end 164 (i.e. the distance of the bend from the application side end of shaft 144) and by varying location of placement and angle of attachment of cam plate 154 to transducer 28. Additionally, the configuration and location of slot 158 can be varied (and/or the size of cam plate 154 can be varied). For example, the pivot range can be increased by moving cam plate 154 closer toward the control side of transducer 28 and/or moving bent end 164 along the rotation axis closer to the control side of device 20. In that case, the shorter distance between cam plate 154 and the pivot axis results in a greater displacement of transducer 28 due to the larger proportional difference in distances as measured from the pivot axis to bent end 164 between the zero displacement position and the maximum displacement position. As another example, bent end 164 can be enlarged in order to increase the pivot range.

The embodiment of FIG. 8 can have pivot range and amplitude which is adjustable by the user so that uninteresting regions may be omitted from the imaged volume to increase frame rate. Motor 33 can be disposed within catheter 22 such that is movable in an axial direction along the rotation axis. In that case, a tension wire is attached to the control side of motor 33 and extends through catheter 22 to a user-actuated rotational knob or other tensioning device. The user can rotate the knob causing the tension wire to wrap around a portion of the knob which shortens the tension wire and applies a force to the control side of motor 33 and causes motor 33 to move axially relative to the rotation axis in the control side direction. This movement acts against the direction of force acting upon the motor from bias force member 142 which increases the tension force acting upon motor 33. Similarly, the user can rotate the knob in the opposite direction which lengthens the tension wire and allows motor 33 to move axially in the application side direction under the tension force of bias force member 142. By moving motor 33 axially toward the control side of device 20, the amplitude and range can be increased by causing bent end 164 to engage surfaces 162, 163 generally at a point which is further from the rotation axis such that slot 158 (and likewise transducer 28) undergoes increased displacement when bent shaft 144 rotates.

In the FIG. 8 embodiment, the fluid surrounding transducer 28 can also provide lubrication between bent shaft 144 and shaft 140 as well as to bias force member 142. The fluid can be preassembled or added before use as described above.

The embodiments described herein allow device 20 to include a directly rotating transducer element which avoids the need for use of a rotating mirror design and the disadvantages associated with such design. For example, the device 20 is shorter and takes up less space than a rotating mirror design. The directly rotating transducer embodiments described herein have a deeper acoustic focal depth than a rotating mirror design. In the disclosed embodiment, ultrasound waves are transmitted directly in the direction of interest as opposed to a reflector design in which ultrasound waves must travel toward a reflector for several millimeters before beginning to travel in the direction of interest.

Device 20 facilitates capture of an image through a viewing window which is free from unnecessary acoustic attenuation such as artifacts, obstructions, or errors within the image. For example, positioning of transducer 28 at a location which is on an application side of the rotary motor 32, conductors 50, 52, and other components, ensures that wires or other echogenic materials are not positioned within or across the viewing window of transducer 28, even as transducer 28 rotates in a full 360° rotation about the rotation axis as well as pivoting about the pivot axis. In this way, there are no wires or other reflecting materials which could cause artifacts within the image or block portions of the redirected ultrasound waves. This provides the physician a clear view of the entirety of the viewing window. Placing wires or other conductors 50, 52 through lumens 72, 73 of shafts 70, 71 also permits a reduction in the overall width of device 20, as no extra space need be provided for such conductors on the periphery of the device. As used herein, the term "window" includes a substantially obstruction-free pathway throughout the structure of device 20 between transducer 28 and organic fluids or tissue which may be positioned external to device 20 during use.

Device 20 is configured to be used with existing medical devices which are designed for percutaneous, intraluminal, or interstitial procedures. For example, device 20 can be used as or with a variety of catheters for different purposes, e.g. positioned on or within an application side of a catheter, depending on the particular configuration. Parts of device 20 as previously described can be positioned within an existing lumen within the catheter. In an alternative embodiment, device 20 could include an external casing which is similar to catheter 22 having walls 24 but being shortened so as to compactly contain device 20. Device 20 could be mounted externally to a catheter using a variety of mounting devices, glues or other types of arrangements. It will be understood by those skilled in the art that the particular type of mounting procedure for the device 20 to an existing medical device can include a variety of different types of mounting methods. Accordingly, the particular methods described herein are not indicative of any limiting aspects of the usage capabilities of the device 20.

In some embodiments described herein, hall sensors (not shown), optical encoders (not shown), ultrasound, back EMF, motor saliency, or a combination of one or more of these may be used to control and/or monitor angular positions of the motors. It has been determined that hall sensors are advantageous as a feedback mechanism because of their small size and mature design. In some embodiments, the ultrasound beam or signals emitted and/or received by transducer 28 is used as a feedback mechanism to precisely assess or monitor the rotational position of rotary motor 32 (and the ultrasound beam rotated by it) relative to the rest of device 20, ensuring proper registration of images obtained through transducer 28. Other features may be included with the embodiments noted herein such as indexing systems and three-dimensional ultrasound devices.

While some of the above discussion concerned specific use in the context of ultrasound system applications, it will be understood that embodiments of device 20 could also be used for a variety of other medical procedures and with a variety of other medical devices. The versatility of the embodiments described herein allows device 20 to be used to guide percutaneous therapeutic interventions such as, for example, embolism coils, stents, filters, graphs, balloons, biopsies, and ministering therapeutics, etc. Device 20 can be used to locate various anatomical landmarks that will be used to correctly place or guided therapy. Typical landmarks include confluences, bifurcations, side branches, nearby vessels, nearby nerves, the heart, and other tissues adjacent to vessels or other orifices containing the transducer. Device 20 can also be used to locate diseased tissue that will be treated or avoided. Device 20 can be used during a biopsy to provide an image of a needle being deployed into tissue. During a TIPS (transjugular intrahepatic portocaval shunt) procedure an image can be produced to allow a physician to watch a needle being placed into the portal vein. For AAA (aortic abdominal aneurysm) graft delivery, device 20 can allow a physician to place a guidewire into a contralateral leg. Device 20 could also be used to image the location of a deployed implantable device both during and after deployment.

Although particular materials were highlighted herein for some components of the device 20, those materials are not intended to be limiting of the types of materials which are suitable to be used in the device 20. Additionally, where materials were not highlighted, a variety of materials could be used such as certain types of metals, polymers, ceramics or other types of materials which are suitable for use in devices for subcutaneous use as well as IVUS imaging procedures.

The device 20 could also be used for a variety of other medical procedures and with a variety of other medical devices. It will be understood by those skilled in the art that the particular type of mounting procedure can include a variety of different types of mounting methods. Accordingly, the particular methods described herein are not indicative of any limiting aspects of the usage capabilities of the device 20.

In the use of the terms "rotation" or "rotational," e.g. with respect to a rotational axis, it should be understood that even though rotation often implies an angle change much greater than 360°, the devices disclosed herein may be configured in certain embodiments so that the rotational angle may rotate through angles less than 360°. In some instances the term "pivot" may be considered by some more natural than "rotate" or vice versa, but for the purposes of this application the terms "rotate" and "pivot" are used for clarity to indicate the axis about which a change in angle occurs, not the nature or magnitude of the angle change.

While the disclosure has been illustrated and described in detail in the drawings and foregoing description, the same is to be considered as illustrative and not restrictive in character, it being understood that only preferred embodiments have been shown and described and that all changes, equivalents, and modifications that come within the spirit of the subject matters defined by the following claims are desired to be protected. It will be understood that structures or other features described with respect to one particular embodiment or item may be used in connection or along with other features, items or embodiments included herein. All publications, patents, and patent applications cited in this specification are herein incorporated by reference as if each individual publication, patent, or patent application were specifically and individually indicated to be incorporated by reference and set forth in its entirety herein.

What is claimed is:

1. A medical device, comprising:
    a unidirectional rotary motor;
    a bidirectional ultrasound transducer; and
    a unidirectional-to-bidirectional gear assembly operatively disposed between the motor and the transducer and configured to convert unidirectional rotational motion into bidirectional rotational motion.

2. The device of claim 1, wherein the transducer is configured for transmitting and/or receiving ultrasound signals;
    wherein the rotary motor is operatively coupled with a first drive shaft, wherein the first drive shaft extends substantially along a rotation axis, and wherein operation of the motor rotates the drive shaft about the rotation axis;
    wherein the gear assembly comprises an internal gear and first and second external gears, wherein the first external gear is interengaged with the second external gear, wherein the internal gear is positioned to rotate about the rotation axis, wherein the gear assembly is operatively coupled with the first drive shaft and the transducer; and wherein the internal gear has a first toothed portion and a first untoothed portion and is disposed so that during rotation of the internal gear the first toothed portion alternately engages the first and second external gears.

3. The device of claim 2, further comprising a diametric first external gear and a diametric second external gear, wherein the diametric first external gear is positioned diametrically opposite to the first external gear and the diametric second external gear is positioned diametrically opposite to the second external gear, wherein the diametric first external gear engages both the second external gear and the diametric second external gear, and wherein the diametric second external gear engages both the first external gear and the diametric first external gear, and wherein a radially central aperture exists between the external gears and intersects the rotation axis.

4. The device of claim 3, further comprising a conduction pathway, wherein the conduction pathway extends from the transducer through the aperture.

5. The device of claim 4, further comprising a second drive shaft operatively disposed between the transducer and the gear assembly, wherein the first drive shaft includes a first lumen running therethrough and wherein the second drive shaft includes a second lumen running therethrough, wherein the first drive shaft is operatively connected with the internal gear, and wherein the conduction pathway extends from the transducer through the second and first lumens.

6. The device of claim 5, the gear assembly further comprising a third external gear and a driving gear, wherein the third external gear is disposed to rotate coaxially and in response to rotation of the second external gear, wherein the driving gear is interengaged with the third external gear and is disposed to rotate about the rotation axis, and wherein the second drive shaft is operatively connected with the driving gear.

7. The device of claim 3, wherein the internal gear further comprises a second toothed portion positioned radially opposite of the first toothed portion, wherein the first and second toothed portions have an arc length defined by the formula $L=\theta r$, where r is a radius measured from the rotation axis to toothed portion, and wherein $\theta \leq 90°$.

8. The device of claim 2, further comprising a third external gear and a driving gear, wherein the third external gear is disposed to rotate coaxially and in response to rotation of the second external gear, and wherein the driving gear is interengaged with the third external gear.

9. The device of claim 8, further comprising a second drive shaft and a conduction pathway, wherein the first drive shaft is operatively connected with the internal gear, and wherein the second drive shaft is operatively connected between the driving gear and the transducer.

10. The device of claim 1, wherein the medical device is mounted in a catheter.

11. The device of claim 1, wherein the transducer rotates reciprocatingly through a range of at least 360° in each direction.

12. The device of claim 2, further comprising a frictional interface fixed relative to the internal gear, wherein the frictional interface is positioned to absorb rotational energy from the first and second external gears during rotation of the internal gear.

13. The device of claim 12, further comprising a non-toothed disc connected to one or more of the first and second external gears so that the non-toothed disc rotates in response to rotation of one or more of the first and second external gears, wherein the non-toothed disc is positioned to engage the frictional interface.

14. A medical device including an elongated member, comprising:
a first motor operatively coupled with a first drive shaft extending along a length of the elongated member, wherein the first drive shaft extends substantially along a rotation axis, wherein operation of the first motor rotates the first drive shaft about the rotation axis;
a transducer configured for transmitting and/or receiving ultrasound signals, wherein the transducer is disposed to move about a pivot axis which is substantially perpendicular to the rotation axis; and
wherein the first drive shaft includes a cam surface disposed to impart pivotal motion to the transducer when the first drive shaft rotates.

15. The device of claim 14, further comprising an elongated slot positioned to receive the cam surface, wherein the cam surface is positioned on a part of the first drive shaft which is bent at an angular offset relative to the rotation axis.

16. The device of claim 15, further comprising a cam plate, wherein the elongated slot is situated in the cam plate, and wherein the cam plate extends from a surface of the transducer.

17. The device of claim 14, further comprising a second motor operatively coupled with a second drive shaft, wherein the second drive shaft extends substantially along the rotation axis, and wherein operation of the second motor rotates the second drive shaft about the rotation axis, wherein the transducer is operatively connected with the second drive shaft, and wherein a difference between the rotational speed of the first motor and the rotational speed of the second motor determines the speed of movement of the transducer about the pivot axis.

18. The device of claim 17, wherein the second drive shaft has a lumen extending therethrough and wherein the first and second drive shafts are positioned concentrically.

19. The device of claim 14, wherein the first motor is axially movable along the rotation axis, and wherein movement of the first motor along the rotation axis changes the range of motion of the transducer about the pivot axis.

20. A medical device comprising:
a transducer configured for transmitting and/or receiving ultrasound signals;
a first motor operatively disposed to impart movement to the transducer about a pivot axis which is substantially perpendicular to a rotation axis;
a second motor operatively disposed to impart rotational motion to the transducer about the rotation axis; and
wherein the speed of movement of the transducer about the pivot axis is determined by a difference between the rotational speed of the first motor and the rotational speed of the second motor.

21. The device of claim 20, wherein the first motor is operatively coupled with a first drive shaft, wherein the first drive shaft extends substantially along the rotation axis, wherein operation of the first motor rotates the first drive shaft about the rotation axis; wherein the second motor is operatively coupled with a second drive shaft, wherein the second drive shaft extends substantially along the rotation axis, wherein operation of the second motor rotates the second drive shaft about the rotation axis; and wherein the transducer is pivotally connected to the second drive shaft.

22. The device of claim 21, wherein the second drive shaft has a lumen extending therethrough and wherein the first and second drive shafts are positioned concentrically.

23. The device of claim 20, wherein the first motor is operatively coupled with a first drive shaft, wherein the first drive shaft extends substantially along the rotation axis, wherein operation of the first motor rotates the first drive shaft about the rotation axis, wherein the first drive shaft includes a cam surface disposed to impart pivotal motion to the transducer when the first drive shaft rotates.

24. The device of claim 23, wherein the second motor is operatively coupled with a second drive shaft, wherein the second drive shaft extends substantially along the rotation axis, wherein operation of the second motor rotates the second drive shaft around the rotation axis, and wherein the transducer is pivotally connected to the second drive shaft.

25. The device of claim 23, further comprising an elongated slot positioned to receive the cam surface, wherein the cam surface is positioned on a part of the first drive shaft which is bent at an angular offset relative to the rotation axis.

26. The device of claim 25, further comprising a cam plate, wherein the elongated slot is situated in the cam plate, and wherein the cam plate extends from a surface of the transducer.

27. The device of claim 26, wherein the second motor is operatively coupled with a second drive shaft, wherein the second drive shaft extends substantially along the rotation axis, wherein operation of the second motor rotates the second drive shaft about the rotation axis; and wherein the transducer is pivotally connected to the second drive shaft.

28. The device of claim 20, wherein the first motor is movable along the rotation axis, and wherein movement of the first motor along the rotation axis changes the range of motion of the transducer about the pivot axis.

* * * * *